United States Patent [19]

Karmas

[11] 3,936,493
[45] Feb. 3, 1976

[54] DIARYLMETHYLENES
[75] Inventor: George Karmas, Bound Brook, N.J.
[73] Assignee: Ortho Pharmaceutical Corporation, Raritan, N.J.
[22] Filed: Apr. 17, 1973
[21] Appl. No.: 351,940

[52] U.S. Cl. ... 260/488 CD; 260/327 M; 260/340.9; 260/468 K; 260/479 R; 260/514 K; 260/613 R; 260/618 R; 424/311; 424/341; 424/343; 260/590 C; 260/590 D
[51] Int. Cl.² .................. C07C 69/02; C07C 69/14
[58] Field of Search ..... 260/618 R, 488 CD, 613 R, 260/479 R, 619 A, 619 D

[56] References Cited
OTHER PUBLICATIONS
Treibs et al., Berichte 91, pp. 2282–2289, (1958).

Primary Examiner—Lorraine A. Weinberger
Assistant Examiner—Jane S. Myers
Attorney, Agent, or Firm—Benjamin F. Lambert

[57] ABSTRACT

Novel diarylmethylenyl cyclohexane carbinols and esters thereof and methods of preparing these novel compounds are described. The novel compounds are useful as antilittering agents.

6 Claims, No Drawings

DIARYLMETHYLENES

BACKGROUND OF THE INVENTION

This invention relates to a new class of chemical compounds having utility as antilittering agents. The novel compounds are diarylmethylenyl cyclohexane carbinols and esters thereof and are typified by compounds having the following molecular structure:

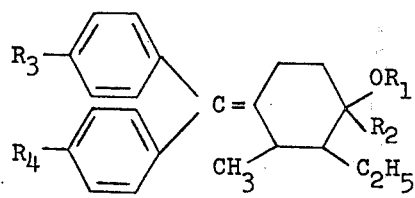

wherein $R_1$ is hydrogen or —COR wherein R is lower alkyl of from 1 to 5 carbon atoms such as methyl, ethyl, propyl, isopropyl, butyl and the like; $R_2$ is hydrogen, a lower alkyl group of from 1–5 carbon atoms or a lower alkynyl group of from 2–5 carbon atoms such as ethynyl, propynyl, butynyl and the like; $R_3$ and $R_4$ are hydrogen, a lower alkyl group of from 1–5 carbon atoms, a lower alkoxy group of from 1–5 carbon atoms such as methoxy, ethoxy, propoxy, isopropoxy, butoxy and the like or a lower alkanoyloxy group of from 2–5 carbon atoms such as acetoxy, propionyloxy and the like. Preferred among the compounds represented above are those wherein R is lower alkyl and $R_3$ and $R_4$ are each hydrogen, although those compounds wherein $R_3$ and $R_4$ are lower alkoxy and lower alkanoyloxy also show good activity. The most preferred compound of the present invention is 1-(diphenylmethylenyl)-2-methyl-3-ethyl-4-acetoxycyclohexane.

The novel diarylmethylenyl cyclohexane carbinol esters and derivatives of the present invention can be prepared by reacting an appropriately substituted, protected cyclohexanone with a Grignard reagent carrying the desired aryl moiety of the final compound. Suitable protecting groups for the cyclohexanone include ketals such as the cyclic ethylene ketal and thioketals such as the cyclic ethylene thioketal. The resulting condensation product is then dehydrated, preferably in a strong acid catalyzing system, to effect formation of the methylene bridge. Suitable acid catalysts include p-toluenesulfonic acid, hydrochloric acid, sulfuric acid and the like. The acid-catalyzed reaction has no stereochemical affect on the alkyl groups. The ketone protecting group is then removed and the cyclohexanone compound which forms is a useful intermediate which also possesses some antilittering activity. The preferred reagent for regenerating the ketone from the protecting group is a mixture of mercuric chloride and cadmium carbonate. The cyclohexanone intermediate is then reduced to the hydroxy compound with an appropriate reducing agent such as a complex metal hydride. Suitable complex metal hydrides are lithium aluminum hydride, sodium borohydride and the like. The final step is an esterification process whereby the hydroxy group is converted to the appropriate ester function using standard esterification techniques.

The thioketals which are used as the starting materials in the preparation of the novel diarylmethylene cyclohexane carbinol esters are themselves novel compounds as are all of the compounds obtained during each step of the reaction sequence. The starting materials may be prepared in accordance with the procedures set forth in the Examples hereinafter presented.

It will be appreciated by those skilled in the art that stereochemical considerations may be encountered in the reaction sequence. It is an advantage of the present process, however, that the stereochemical relations of the groups are retained in the Grignard reactions and in the neutral process of regenerating the ketones from the thioketals. The compounds prepared by the above-described process have cis-methyl and cis-ethyl configurations relative to the ester moiety.

Alternatively the thioketal hydroxy compound may be first converted to an hydroxy cyclohexanone derivative as described above, followed by dehydration with strong acid. When this method is employed, however, some epimerization of the 3-ethyl group takes place.

As stated previously, the compounds of the present invention exhibit antilittering activity. In addition, the intermediates used in preparation of the novel diarylmethylenyl cyclohexane derivatives also exhibit antilittering activity in varying degrees.

The novel diarylmethylenyl cyclohexane derivatives of this invention differ in this regard from the closest prior art of which applicant is aware, namely U.S. Patent No. 3,287,397, dated November 22, 1966. In the above-noted patent, compounds having a bis-(alkoxyphenyl, benzyloxyphenyl and hydroxyphenyl) methylenyl cyclohexane moiety are disclosed together with some analogs thereof, wherein the cyclohexane moiety is alkyl substituted. This prior art, however, does not disclose compounds having the activity of the instant compounds nor does it disclose compounds wherein the cyclohexane moiety carries either the free carbinol or an esterified carbinol at the position para to the methylene bridge.

In the examples which appear hereinbelow, antilittering actitity is determined as follows:

A test group of rats is fed a calculated amount of a test substance in the feed for a period of 7 days during which time males and females are kept separate with both sexes receiving the test substance. Thereafter, the males and females are cohabited and the diet fed is continued for 15 days. At the end of this time, the cohabitation is ended and the drug removed from the diet. The females are then observed for a period of 21 days and are allowed to deliver their young, if any, and to raise them. A control group of rats is handled in precisely the same way at the same time except that their diet does not include the test substance.

As mentioned above, the compounds of the invention also exhibit post-coital antilittering effects when administered on days 9 through 12 after coitus in one single, oral dose per day. The effect is measured by determining the percent resorption of conceptuses at a particular dosage level. The novel compounds have been found to be effective when administered at dosage levels of from at least 0.5 mg/kg to about 25 mg/kg.

The following examples are given to illustrate specific and preferred embodiments of the present invention:

EXAMPLE 1

1-Diphenyl 2-methyl-3-ethyl-4-acetoxycyclohexane

To a stirred suspension of 1.0 g. of lithium aluminum hydride in 30 ml. of tetrahydrofuran is added, portionwise, a total of 2.0 g. of 1-diphenylmethylenyl-2-methyl-3-ethyl-4-ketocyclohexane. The resulting mixture is stirred at 25° C. for 40 minutes, after which it is poured into a cold stirred mixture of 10 ml. of 20% aqueous sodium hydroxide, 10 ml. of saturated brine and 100 ml. of ethyl ether. The hydrolysis mixture is stirred at 25° C. for 40 minutes, filtered to remove inorganic solids and the filtrate layers are separated. The ether phase is washed with water, dried over magnesium sulfate and upon evaporation 2.0 g. of 1-diphenylmethylenyl-2-methyl-3-ethyl-4-hydroxycyclohexane are obtained as a viscous oil. The crude carbinol is dissolved in a mixture of 25 ml. of pyridine and 3 ml. of acetic anhydride and the resulting solution is maintained at 90° C. for 5 hours. The solution is then cooled to 15° C., diluted with 100 ml. of water and extracted with 30 ml. of hexane. The hexane solution is successively washed with cold dilute hydrochloric acid, water and sodium bicarbonate, dried over magnesium sulfate and evaporated to an oily residue. The residue is chromatographed on neutral alumina, and the column is eluted with a 10% ether-90% hexane solution. The eluates are combined and evaporated to yield 1.6 g. of crystalline material. Upon two recrystallizations from aqueous methanol 0.85 g. of the 2,3-cis-3,4-cis isomer of 1-diphenylmethylenyl-2-methyl-3-ethyl-4-acetoxycyclohexane, are obtained as fine white prisms, m.p. 91°–92° C.

$\lambda\lambda$ max: 3.28, 3.31, 5.75, 7.28, 8.08, 9.20-9.30, 14.30$\mu$ (CCl$_4$)

EXAMPLE 2

1-[di-(p-Anisyl)methylenyl]-2-methyl-3-ethyl-4-acetoxycyclohexane

A solution of 1.5 g. of lithium aluminum hydride in 40 ml. of tetrahydrofuran is stirred at 0° C. and to it is added a solution of 2.8 g. of 1-[di-(p-anisyl)methylenyl]-2-methyl-3-ethyl-4-ketocyclohexane in 20 ml. of tetrahydrofuran over a period of 5 minutes. The reaction mixture is stirred at 25° C. for 90 minutes after which it is cooled in ice. The excess lithium aluminum hydride is destroyed by the cautious addition of 5 ml. of 10% aqueous sodium hydroxide, followed by 10 ml. of saturated aqueous sodium sulfate. After the evolution of hydrogen has ceased, the mixture is filtered, and the filter cake is washed thoroughly with ether. The ether phase of the filtrate is separated, dried over magnesium sulfate, filtered and evaporated to yield 1-[di-(p-anisyl)methylenyl]-2-methyl-3-ethyl-4-hydroxycyclohexane as a viscous yellow oil.

The crude carbinol is acetylated by dissolving it in a mixture of 12 ml. of pyridine and 3 ml. of acetic anhydride and heating the resultant solution at 95°–100° for 5 hours. The excess acetic anhydride is hydrolyzed at the addition of water and the acetate is extracted with ether. The ether solution was washed with dilute hydrochloric acid, water, and sodium bicarbonate solution, dried with magnesium sulfate and evaporated to a viscous yellow oil. The oil is purified by distillation under high vacuum to afford 2.6 g. of the 2,3-cis-3,4-cis isomer of 1-[di-(p-anisyl)methylenyl]-2-methyl-3-ethyl-4-acetoxycyclohexane as a yellow glass which distills at 175°–185° at 0.001 mm. The resonances of the 2-methyl and the 4-acetoxy groups in the nuclear magnetic resonance spectrum indicate that the product essentially consists of one isomer.

$\lambda\lambda$ max: 5.78, 8.08, 8.51, 9.68, 10.50, 11.83, 12.08, 13.29$\mu$, (neat).

EXAMPLE 3

1-Diphenylmethylenyl-2-methyl-3-ethyl-4-hydroxycyclohexane Hexanoate

A. A solution of 22.5 g. of ethyl 2-methyl-3-ethyl-4-ketocyclohexanecarboxylate (all-cis form, m.p. 28°–32°) in 450 ml. of methanol is stirred and maintained at a temperature of 5°–7° C. while a total of 11.0 g. of sodium borohydride is added over a period of 40 minutes. The reaction mixture is stirred at 5° C. for an additional one hour after which a total of 40 ml. of acetic acid is added cautiously to neutralize the base. The methanol solution if evaporated under vacuum to a pasty residue which is shaken with ether and water. The ether phase is washed with aqueous sodium bicarbonate and is dried and evaporated to yield a colorless oil. Upon distillation of the oil, 21.5 g. of ethyl 2-methyl-3-ethyl-4-hydroxycyclohexanecarboxylate is obtained as a mobile oil having a boiling point of 88°–91° at 0.001 mm.

The nuclear magnetic resonance spectrum of the oil shows that the hydroxyester is a mixture of 80% 1,2-cis-2,3-cis-3,4-cis isomer and 20% 1,2-cis-2,3-cis-3,4-trans isomer.

B. A solution of 7.6 g. of ethyl 2-methyl-3-ethyl-4-hydroxycyclohexanecarboxylate (prepared as in A above) in 70 ml. of tetrahydrofuran is stirred at 0°–10° C. while 64 ml. of 2.3 molar solution of phenyl lithium is added. The reaction mixture is allowed to stand at 25° C. for 16 hours after which it is poured with stirring into an ice and water mixture which has been layered with 120 ml. of ether. The aqueous phase is separated, reextracted with ether, after which the combined ether solution is washed with water, dried over magnesium sulfate and evaporated to a tacky crystalline residue. The residue is recrystallized from a methylene chloride-carbon tetrachloride mixture to afford 10.35 g. of fine white prisms which melt at 170°–176°. The nuclear magnetic resonance spectrum shows that the product is diphenyl-(2-methyl-3-ethyl-4-hydroxycyclohexanyl-1) carbinol, which is mostly the 1,2-cis-2,3-cis-3,4-cis isomer, containing a few percent of the 1,2-cis-2,3-cis-3,4-trans isomer.

C. To a stirred suspension of 3.0 g. of diphenyl-(2-methyl-3-ethyl-4-hydroxycyclohexanyl-1) carbinol (prepared as in B above) in 50 ml. acetic acid is added 0.4 g. of p-tolunesulfonic acid monohydrate. The resulting clear solution is maintained at 25° for one hour after which it is poured into a mixture of ice and excess 10% ammonium hydroxide, layer with ether. After shaking and separation of the layers, the ether phase is dried over magnesium sulfate and evaporated to afford 2.8 g. of a viscous colorless oil. The nuclear magnetic resonance spectrum shows the oil to be the 2,3-cis-3,4-cis isomer, containing a few percent of the 2,3-cis-3,4-trans isomer.

D. A solution of 2.8 g. of 1-diphenylmethylenyl-2-methyl-3-ethyl-4-hydroxycyclohexane (prepared as in C, above) in a mixture of 7 ml. of pyridine and 5 ml. of hexanoic anhydride is heated at 95°–100° C. for five hours. To this solution is added 1 ml. of water and 3 ml. of pyridine, and the mixture is stirred at 25° C. for 4 hours to hydrolyze excess hexanoic anhydride. The mixture is then diluted with hexane and the hexane phase is washed twice with dilute hydrochloric acid and three times with dilute ammonium hydroxide after which it is dried and evaporated to yield an oily residue.

The residue is then distilled to afford 3.36 g. of 1-diphenylmethylenyl-2-methyl-3-ethyl-4-hydroxycyclohexane hexanoate, a viscous pale yellow oil which boils at 150°–160° C. at 0.001 mm.

λλ max: 5.80, 8.03, 8.51, 9.12, 9.31, 9.70, 10.42, 13.12, 13.32, 14.28μ (neat).

EXAMPLE 4

1-Diphenylmethylenyl-2-methyl-3-ethyl-4-acetoxycyclohexane (2,3-cis-3,4-trans isomer)

To a stirred suspension of 8.0 g. of lithium aluminum hydride in 240 ml. of tetrahydrofuran is added, portionwise, a total of 16.0 g. of 1-diphenylmethylenyl-2-methyl-3-ethyl-4-ketocyclohexane. The resulting mixture is stirred at 25° C. for 40 minutes, after which it is poured into a cold, stirred mixture of 80 ml. of 20% aqueous sodium hydroxide, 80 ml. of saturated brine, and 800 ml. of ethyl ether. The hydrolysis mixture is stirred at 25° C. for 40 minutes, filtered to remove inorganic solids and the filtrate layers are separated. The ether phase is washed with water, dried over magnesium sulfate, and upon evaporation 16.0 g. of 1-diphenylmethylenyl-2-methyl-3-ethyl-4-hydroxycyclohexane are obtained as a viscous oil. The crude carbinol is dissolved in a mixture of 200 ml. of pyridine and 24 ml. of acetic anhydride and the resulting solution is maintained at 90° C. for 5 hours. The solution is then cooled to 15° C., diluted with 800 ml. of water and extacted with 240 ml. of hexane. The hexane solution is successively washed with cold dilute hydrochloric acid, water and sodium bicarbonate, after which it is dried over magnesium sulfate and evaporated to an oily residue. The residue is chromatographed on neutral alumina and the column is eluted with a 10% ether-90% hexane solution. The eluates are combined and evaporated to yield 12.8 g. of crystalline material. Upon two recrystallizations from aqueous methanol, 6.8 g. of the 2,3-cis-3,4-cis isomer of 1-diphenylmethylenyl-2-methyl-3-ethyl-4-acetoxycyclohexane are obtained as fine white prisms, m.p. 91°–92°. The mother liquors are combined and evaporated to a viscous oil which crystallizes from methanol. Five small successive crops are taken as the volume of methanolic mother liquor is diminished by evaporation. The first two crops are mostly the 2,3-cis-3,4-cis isomer and melt in the range of 86°–94° C. The last three crops, which total 0.65 g., are mostly the 3,4-trans isomer and melt in the range of 112°–135° C. The higher-melting portions are combined and are recrystallized twice from methanol to afford 0.30 g. of the 2,3-cis-3,4-trans isomer of 1-diphenylmethylenyl-2-methyl-3-ethyl-4-acetoxycyclohexane as white, dense granules, m.p. 140°–142° C.

λλ max: 5.76, 8.04, 9.60, 9.70, 10.29, 14.28μ(CCl$_4$)

The 3,4-trans isomer is readily distinguished from the cis isomer by NMR spectroscopy. The doublet of the 2-methyl group of the 3,4-trans isomer has a chemical shift value (δ, in CDCl$_3$) smaller than that of the 3,4-cis isomer.

EXAMPLE 5

1-Diphenylmethylenyl-2-methyl-3-ethyl-4-methyl-4-acetoxycyclohexane

A mixture of 1.8 g. of 1-diphenylmethylenyl-2-methyl-3-ethyl-4-hydroxy-4-methylcyclohexane and 15 ml. of acetic anhydride is refluxed for 10 hours and then it is evaporated under high vacuum to a viscous oil of the crude acetate. The oil is chromatographed on silicic acid, eluting with benzene, to separate the acetate from unacetylated carbinol. The portions containing the acetate are combined and upon recrystallization from a small amount of methanol 1.1 g. of 1-diphenylmethylenyl-2-methyl-3-ethyl-4-methyl-4-acetoxycyclohexane are obtained as fine white granules, m.p. 88°–89°C.

λλmax: 5.79, 8.05, 8.39, 8.54, 8.90, 9.78, 11.32, 13.09, 14.25μ (KBr).

EXAMPLE 6

1-Diphenylmethylenyl-2-methyl-3-ethyl-4-acetoxy-4-ethynylcyclohexane

A solution of 1.3 g. of 1-diphenylmethylenyl-2-methyl-3-ethyl-4-hydroxy-4-ethynylcyclohexane in 30 ml. of tetrahydrofuran is stirred at 5° C. and to it is added 1.7 ml. of a 2.3 molar ethereal solution of methyl lithium, followed by 0.38 ml. of acetic anhydride After 10 minutes, water is added to the reaction mixture and the ether phase separated, dried and evaporated to a viscous oil. Upon crystallization from hexane, 1.1 g. of 1-diphenylmethylenyl-2-methyl-3-ethyl-4-acetoxy-4-ethynylcyclohexane are obtained as fine white prisms, m.p. 126°–127° C.

λλmax: 3.07, 5.78, 8.12, 9.34, 9.81, 10.51, 11.12, 12.92, 13.09, 13.21, 14.26μ (KBr).

EXAMPLE 7

1-Diphenylmethylenyl-2-methyl-3-ethyl-4-hydroxy-4-methylcyclohexane 2,3-cis-3,4(OH)-cis A solution of 4.0 g. of 1-diphenylmethylenyl-2-methyl-3-ethyl-4-ketocyclohexane in 80 ml. of tetrahydrofuran is stirred at −20°C. while 23 ml. of a 2.3 molar ethereal solution of methyl lithium is added. The reaction mixture is allowed to stand at 25° C. for 18 hours and then it is again cooled to −20° and stirred while 100 ml. of ether, followed by 40 ml. of water, is added. After separation of layers, the organic phase is washed with water, dried with magnesium sulfate, and evaporated to a viscous pale yellow oil. The latter is dissolved in hexane and the solution is chilled to afford, in three crops, a total of 2.4 g. of large cream granules. The entire 2.4 g. is dissolved in 50 ml. of hexane, with stirring, at 25° C. and the solution is filtered to remove a small amount of insoluble matter. The filtrate is reduced to a volume of 8 ml., seeded, and stored at 0° C. to afford 1.6 g. of 1-diphenylmethylenyl-2-methyl-3-ethyl-4-hydroxy-4-methylcyclohexane, large white granules which melt at 70°–71°C.

The nuclear magnetic resonance spectrum indicates that the product is essentially a single isomer, the 2,3-cis-3,4(OH)-cis.

λλmax: 2.80, 8.40, 9.22, 9.31, 10.98, 11.08, 11.37, 12.64, 13.03, 13.16, 14.32μ (KBr).

EXAMPLE 8

1-[di-(p-Acetoxyphenyl)methylenyl]-2-methyl-3-ethyl-4-acetoxycyclohexane

A. A solution of 4.5 g. of 1-[di-(p-acetoxyphenyl)methylenyl]-2-methyl-3-ethyl-4-ketocyclohexane in 90 ml. of tetrahydrofuran is stirred and maintained at 10°–20°C. while a total of 9.0 g. of lithium aluminum hydride is added over a period of 20 minutes. The resulting mixture is refluxed with stirring for one hour and then chilled in ice and water. A 5% aqueous hydrochloric acid solution is added to the cold mixture until an acidic pH is attained. The mixture is extracted with two 100 ml. portions of ether and the combined ether extracts are dried over anhydrous magnesium sulfate. Upon evaporation of the ether, 4.0 g. of 1-[di(p-hydroxyphenyl)methylenyl]-2-methyl-3-ethyl-4-hydroxycyclohexane are obtained as a glassy residue.

λλmax: 2.9- 3.2, 6.22, 6.65, 6.97, 7.9-8.2, 9.10, 9.50, 12.00μ (neat:melted glass).

B. The 1-[di-(p-hydroxyphenyl)methylenyl]-2-methyl-3-ethyl-4-hydroxycyclohexane (4.0 g.), prepared as described in A above, is acetylated by heating it in 25 ml. of pyridine and 15 ml. of acetic anhydride at 95°-100° C. for 3 hours. The resulting solution is poured onto 600 g. of a mixture of ice and water, layered with 150 ml. of ether and this mixture is stirred for 30 minutes to hydrolyze the excess acetic anhydride. After separation of the layers, the ethereal phase is successively washed with 6N hydrochloric acid, water, 10% aqueous sodium bicarbonate, and again with water. The ether solution is then dried and upon evaporation an oily residue is obtained which crystallizes from a mixture of ether and hexane as white granules. A second recrystallization from ether-hexane yields 2.1 g. of 1-[di-(p-acetoxyphenyl)methylenyl]-2-methyl-3-ethyl-4-acetoxycyclohexane, m.p. 139°-143° C.

λλmax: 3.30, 5.70, 5.78, 6.26, 6.67, 7.31, 8.05, 8.20, 8.28, 8.40, 8.60, 9.80, 11.00, 11.70μ (KBr).

EXAMPLE 9

1-Diphenylmethylenyl-2-methyl-3-ethyl-4-hydroxy-4-ethynylcyclohexane: 2,3-cis-3,4(OH)-cis To 200 ml. of dioxane, previously saturated with acetylene gas, is added 9.0 g. of 1-diphenylmethylenyl-2-methyl-3-ethyl-4-ketocyclohexane and 36 g. of lithium acetylide-ethylenediamine complex. Acetylene is bubbled through this mixture for one hour, and then it it stirred at 25°C. for 20 hours. After it has been chilled in ice, the reaction mixture is diluted with 300 ml. of ether and cautiously treated with 200 ml. of a 10% aqueous ammonium chloride solution. After separation of the layers, the ether phase is dried with magnesium sulfate and evaporated to a viscous brown oil. The oil is then chromatographed on neutral alumina and elution with ether and ether plus 10% ethyl acetate affords 6.0 g. of a viscous oil. The infrared spectrum shows the oil to be a mixture of unreacted starting ketone and the desired ethynyl carbinol. This mixture is boiled under reflux for 40 minutes in a mixture of 100 ml. of methanol, 3.0 g. of semicarbazide hydrochloride and 3.0 g. of sodium acetate. Most of the methanol is removed under vacuum and the residue is shaken with ether and water. The ether phase is dried and evaporated, and the oily residue is chromatographed on neutral alumina. Elution with ethyl ether containing 20% ethyl acetate affords 3.5 g. of a crystalline product. The infrared spectrum shows the crystalline material to be ethynylcarbinol free of ketone and semicarbazone. Recrystallization from ether-hexane affords a total of 2.2 g. of 1-diphenylmethylenyl-2-methyl-3-ethyl-4-hydroxy-4-ethynylcyclohexane as white prisms, m.p. at 121°-122° C.

The nuclear magnetic resonance spectrum indicates that this product is a single isomer, the 2,3-cis-3,4(OH)-cis compound.

λλmax: 2.79, 3.04, 8.89, 9.31, 9.50, 9.68, 10.50, 10.89, 13.10, 14.20, 14.74, 15.23μ (KBr).

PREPARATION OF INTERMEDIATES

I

1-Diphenylmethylenyl-2-methyl-3-ethyl-4-ketocyclohexane

A mixture of 2.0 g. of 1-diphenylmethylenyl-2-methyl-3-ethyl-4,4-ethylenedithiocyclohexane, 3 g. of cadmium carbonate, 3 g. of mercuric chloride, 10 ml. of water and 200 ml. of acetone is stirred at 25°C. for 24 hours. An additional 2 g. each cadmium carbonate and mercuric chloride is added and the resultant mixture is stirred for another 24 hours. Then 2 g. each of the above reagents is again added and stirring is continued for a final 24 hours. After filtration, the acetone solution is evaporated to dryness and the residue is leached with 100 ml. of methylene chloride and filtered. The methylene chloride solution is shaken with 150 ml. of 5% ammonium hydroxide and filtered on a wide funnel to remove inorganic solids. The solvent is evaporated to a white solid and the solid is recrystallized from methanol to afford 1.4 g. of 1-diphenylethylenyl-2-methyl-3-ethyl-4-ketocyclohexane as white granules, m.p. 105°-106°C.

λλmax: 5.84, 6.70, 6.92, 8.25, 9.13, 10.49, 11.71, 12.92, 13.13, 14.12-14.20μ(KBr).

II

1-Diphenylmethylenyl-2-methyl-3-ethyl-4,4-ethylenedithiocyclohexane

A. To a solution of 10 g. of 2-methyl-3-ethyl-4-ketocyclohexanecarboxylic acid (all-cis isomer, m.p. 100°-103°) in 10 ml. of 1,2-ethanedithiol is added 10 ml. of a 1.4 N. ethereal solution of hydrogen chloride. The resulting mixture is held at 25°-30°C. for 3 hours after which it is diluted with 50 ml. of nitromethane, chilled at 0°C. for one hour and filtrated to isolate 4.75 g. of 2-methyl-3-ethyl-4, 4-ethylenedithiocyclohexanecarboxylic acid as white prisms, m.p. 168°-173°C. A sample melting at 176°-177° is obtained upon recrystallization from methanol.

B. To a solution of 5 g. of the acid, prepared as in A above, in 100 ml. of methanol is added 25 ml. of 10% methanolic sodium hydroxide and 200 ml. of dimethylformamide. The resulting solution is evaporated to a volume of about 150 ml. and the suspension of the sodium salt is cooled at 10°C., treated with 6 ml. of dimethyl sulfate and then held at 25°C. for 1½ hours. The reaction mixture is then evaporated to a small pasty residue which is shaken with ether and water. The ether phase is separated, washed several times with aqueous potassium carbonate, dried, and evaporated. The residue is crystallized from hexane to afford 4.9 g. of methyl 2-methyl-3-ethyl-4,4-ethylenedithiocyclohexanecarboxylate as white granules, m.p. 66°-67°C.

C. To a stirred solution of 1.0 g. of the thioketal ester, prepared as in B above, in 25 ml. of tetrahydrofuran is added 5 ml. of a 3 M. solution of phenylmagnesium bromide in ether. The reaction mixture is stirred at 50°C. for 1½ hours after which it is cooled, diluted with 50 ml. of ether and hydrolyzed with aqueous ammonium chloride. The ether phase is dried and avaporated and the solid residue obtained is recrystallized from nitromethane to afford 1.2 g. of the tertiary carbinol, diphenyl-(2-methyl-3-ethyl-4,4-ethylenedithiocyclohexanyl-1)carbinol as pale yellow prisms, m.p. 174°–175°C.

D. A mixture of 1.6 g. of the diphenylcarbinol, obtained as in C above, 0.5 g. of p-toluenesulfonic acid, and 25 ml. of acetic acid is stirred at 70°C. for 5 minutes to effect solution and the solution is kept at 25°C. for 20 minutes. The yellow solution is then diluted with 150 ml. of water and extracted with a mixture of ether and hexane. The organic phase is extracted with water and with aqueous potassium carbonate and then dried and evaporated to a viscous residue which is crystallized from hexane to afford 1.3 g. of 1-diphenyl-metehylenyl-2-3-ethyl-4,4-ethylenedithiocyclohexane as white granules, m.p. 120°–121°C.

λλmax: 9.30, 11.12, 12.92, 13.31, 13.49, 14.21μ(KBr).

III

1-[di-(p-Anisyl)methylenyl]-2-methyl-3ethyl-4,4-ethylenedithiocyclohexane

A. To a stirred suspension of 5.0 g. of magnesium turnings in 200 ml. of ether is added, with stirring under gentle reflux, a solution of 13.5 g. of p-bromoanisole in 50 ml. of tetrahydrofuran, over a period of 20 minutes. The resulting solution of p-anisylmagnesium bromide is refluxed for an additional period of 45 minutes after which it is chilled to −45°C. To the cold solution is added with stirring a solution of 4.0 g. of methyl 2-methyl-3-ethyl-4,4-ethylenediethiocyclohexanecarboxylate in 20 ml. of tetrahydrofuran. The reaction mixture is warmed to room temperature and then refluxed for 2 hours. After cooling to −15°C., the mixture is hydrolyzed by the addition of 100 ml. of a half-saturated aqueous solution of ammonium acetate. The magnesium is filtered off and the ether phase of the filtrate is separated and washed with a 5% aqueous sodium hydroxide solution and with water. The ether solution is dried over magnesium sulfate and then evaporated to an oily residue. The residue is crystallized from ether to afford 1.0 g. of [di-(p-anisyl)-2-methyl-3-ethyl-4,4-ethylenedithiocyclohexanyl-1]carbinol as white granules, m.p. 174°–178°C.

λλmax: 2.8–2.9, 6.19, 6.60, 7.99, 8.45, 9.62, 11.10, 11.38, 11.88, 12.06, 12.18 μ(KBr).

B. [di-(p-Anisyl)-2-methyl-3-ethyl-4,4-ethylenedithiocyclohexanyl-1]carbinol (1.0 g.) is dissolved in 25 ml. of acetic acid at 70°C. The solution is then cooled at 25°C. and 120 mg. of p-toluenesulfonic acid monohydrate is added. The resulting solution is then maintained at 25°C. for one hour. After dilution with 100 ml. of water, the acetic acid solution is extracted with a mixture of ether and hexane. The organic phase is washed well with aqueous sodium hydroxide, dried over magnesium sulfate and evaporated to a viscous oily residue. The residue is crystallized from an ether plus hexane mixture to afford 0.7 g. of 1-[di-(p-anisyl)-methylenyl]-2-methyl-3-ethyl-4,4-ethylenedithiocyclohexane as white granules, m.p. 106°–107°C.

λλmax: 3.35, 3.40, 3.50, 6.19, 6.32, 6.60, 8.00, 9.62, 10.92, 11.72, 11.98, 12.08, 12.28μ (KBr).

IV

1-[di-(p-Acetoxyphenyl)methylenyl]-2-methyl-3-ethyl-4-ketocyclohexane

A solution of 4.3 g. of 1-[di-(p-acetoxyphenyl)-methylenyl]-2-methyl-3-ethyl-4,4-ethylenedithiocyclohexane in 300 ml. of acetone is stirred and to it is added 15 ml. of water, followed by 8 g. of mercuric chloride and 8 g. of cadmium carbonate. This mixture is stirred at 25°C. for 24 hours and then filtered. The filtrate is evaporated to a pasty wet residue. The residue is treated with 200 ml. of ether and 100 ml. of a saturated aqueous potassium bicarbonate solution and the resulting mixture is shaken vigorously for several minutes. The brown precipitate which forms is filtered off and the ether phase of the filtrate is separated and washed with 10% ammonium hydroxide. The ether solution is filtered again and then washed with water, dried and evaporated to a viscous oil. Upon crystallization from etherhexane 2.7 g. of 1-[di-(p-acetoxyphenyl)-methylenyl]-2-methyl-3-ethyl-4-ketocyclohexane are obtained as dense cream granules, m.p. 142°–143°C.

λλmax: 5.70, 5.86, 8.23, 8.38, 8.59, 10.99, 11.85, 12.80, 14.92μ(KBr).

V

1-]di-(p-anisyl) -2-methyl-3-ethyl-4-ketocyclohexane

A mixture of 3.0 g. of 1-[di-(p-anisyl)methylenyl]-2-methyl-3-ethyl-4,4-ethylenedithiocyclohexane, 5.0 g. of cadmium carbonate, 3.0 g. of mercuric chloride, 15 ml. of water, and 250 ml. of acetone is stirred for 3 hours at 25°C. An additional 5.0 g. of cadmium carbonate and 5.0 g. of mercuric chloride are added and the resultant mixture is stirred for 20 hours. The mixture is then filtered and the acetone filtrate is evaporated to dryness. The solid residue is leached with 200 ml. of methylene dichloride and the insoluble material is filtered off. The filtrate is washed with 100 ml. of 5% aqueous ammonia and filtered a second time. The methylene chloride filtrate is evaporated to dryness and the residue is recrystallized twice from an ether-hexane mixture to afford 1.3 g. of 1-[di-(p-anisyl)methylenyl]-2-methyl-3-ethyl-4-ketocyclohexane as white granules, m.p. 106°–107°C.

λλmax: 3.35, 5.86, 6.20, 6.35, 6.60, 8.00, 9.62, 12.08, 12.30μ(KBr).

VI

1-[di-(p-Tolyl)methylenyl]-2-methyl-3-ethyl-4-ketocyclohexane

A. The Grignard reagent is prepared in the conventional manner from 26.8 g. of p-bromotoluene and 4.0 g. of magnesium in 125 ml. of ether. The thus prepared Grignard reagent is then stirred at −30°C. and to it is added 10 g. of methyl 2-methyl-3-ethyl-4,4-ethylenedithiocyclohexanecarboxylate (prepared as described above) dissolved in 50 ml. of tetrahydrofuran. The reaction mixture is refluxed for 4 hours and then subjected to conventional hydrolytic workup to afford a glassy ether residue of reaction products. Digestion of the latter with 100 ml. of hexane affords 11.1 g. of di-(p-tolyl)-2-methyl-3-ethyl-4,4-ethylenedithiocyclohexanyl-1 carbinol as fine white granules.

λλmax: 2.88, 8.65, 9.08, 9.81, 12.10, 12.38, 12.80, 13.32μ(KBr).

B. A mixture of 11.0 g. of the carbinol obtained in A (above), 1.0 g. of p-toluenesulfonic acid and 300 ml. of acetic acid is stirred at 25°C. for one hour and then diluted with 1200 ml. of water and extracted with hexane. The hexane phase is washed with aqueous potassium carbonate, dried, and evaporated to a viscous oil. The oil is then redissolved in 30 ml. of hexane. On storage at 0°C., the hexane solution deposits 7.0 g. of 1-[di-(p-tolyl)-methylenyl]-2-methyl-3-ethyl-4,4-ethylenedithiocyclohexane as fine white prisms, m.p. 107°–109°C.

λλmax: 8.43, 0.91, 9.33, 9.79, 11.01, 12.09, 12.22, 12.33, 12.78, 13.49, 13.78μ(KBr).

C. The 4-keto group is regenerated from the unsaturated thioketal obtained in B (above) as described in preparation I above using 7.0 g. of the thioketal and appropriately larger quantities of mercuric chloride, cadmium carbonate, acetone and water. After conventional work-up, the methylene chloride solution of the reaction products is further washed with a 5% aqueous solution of ammonium sulfide before final drying, filtration and evaporation to a viscous oil. The oil is crystallized from ether plus hexane to afford 3.6 g. of 1-[di-(p-tolyl)-methylenyl]-2-methyl-3-ethyl-4-ketocyclohexane as fine white prisms, m.p. 102°–103°C.

λλmax: 5.90, 8.23, 8.48, 8164, 9.02, 9.11, 9.79, 10.60, 12.28, 12.70, 13.63, 13.92, 14.80μ(KBr).

VII

1-[di-(p-Acetoxyphenyl)-methylenyl]-2-methyl-3-ethyl-4,4-ethylenedithiocyclohexane A. The Grignard reagent is prepared in the conventional manner from 50 g. of p-bromophenol tetrahydropyranyl ether and 8.0 g. of magnesium turnings in a mixture of 150 ml. of ethyl ether and 40 ml. of tetrahydrofuran. The thus prepared Grignard reagent is then stirred at −30°C. and to it is added a solution of 12 g. of methyl 2-methyl-3-ethyl-4,4-ethylenedithiocyclohexanecarboxylate in 30 ml. of tetrahydrofuran. The reaction mixture is allowed to stand at 25°C. for 18 hours after which it is diluted with 200 ml. of ether and stirred at −20° while 50 ml. of a 30% aqueous solution of ammonium acetate is added over 15 minutes. A voluminous white precipitate forms and is collected by filtration. The filter cake is washed with ether and water, care being taken to leave the heavier particles of unreacted magnesium in the reaction flask. The filtrate layers are separated and the ether solution is concentrated under vacuum to a pasty residue. The residue is treated with 150 ml. of ether, chilled at 0° C. and filtered to obtain an additional 5 g. of crystalline product. The major portion, after drying in air, weighs 22 g. A total of 27 g. of [di-(p-tetrahydropyranloxyphenyl)-2-methyl-3-ethyl-4,4-ethylenedithiocyclohexanyl-1)] carbinol is obtained. A small portion, upon recrystallization from acetone, is obtained as white microprisms, m.p. 214°–222°C., with decomposition.

λλmax: 2.88, 8.08, 8.50, 9.00, 9.62, 9.78, 10.33, 10.85, 11.90μ(KBr).

B. A mixture of 10.0 g. of the carbinol obtained in A (above), 1.0 g. of p-toluenesulfonic acid and 250 ml. of acetic acid is stirred vigorously at 25°C. for 35 minutes after which 5 ml. of water is added; the stirring is continued for an additional 20 minutes. The acetic acid solution is diluted with 150 ml. of ether and 100 ml. of hexane and then with one liter of water. After vigorous shaking, the aqueous phase is drawn off and the ether phase is washed with 500 ml. of water and then, cautiously, with excess aqueous potassium bicarbonate to remove all of the acetic acid. After drying with magnesium sulfate, the ether solution is evaporated under vacuum to an amorphous glassy froth which is dissolved in 100 ml. of warm chloroform. Upon prolonged storage at 0°C., the chloroform solution slowly deposits 6.0 g. of pale yellow microprisms which melt at 103°–106°C. The product is the dehydrated phenolic compound, 1-[di-(p-hydroxyphenyl)-methylene]-2-methyl-3-ethyl-4,4-ethylenedithiocyclohexane.

λλmax: 3.02, 8.02, 8.21, 8.52, 9.08, 12.01, 13.29μ(KBr).

C. A solution of 5.4 g. of the phenolic thioketal, as obtained in B (above) in 50 ml. of pyridine and 15 ml. of acetic anhydride is allowed to stand at 25° for 2 hours after which the excess acetic anhydride is hydrolyzed by the gradual addition of ice chips. The temperature is kept below 35° during the addition of the ice chips. The acetylation mixture is then diluted with 200 ml. of ether and the ether solution is washed, successively, with 150 ml. of water, two 100 ml. portions of 5% hydrochloric acid, and two 60 ml. portions of 10% potassium carbonate. The ether phase is dried with magnesium sulfate and evaporated to a viscous oil. Upon crystallization from an ether-hexane mixture, 5.1 g. of 1-[di-(p-acetoxyphenyl)methylenyl]-2-methyl-3-ethyl-4,4-ethylenedithiocyclohexane is obtained as white granules, m.p. 154°–156°C.

λλmax: 5.69, 8.3–8.4, 8.59, 9.81, 11.02, 11.75, 15.02μ(KBr).

VIII

2-Methyl-3-ethyl-4-ketocyclohexanecarboxylic acid: all-cis isomer

Crude 2-methyl-3-ethyl-4-ketocyclohexanecarboxylic acid, as described in *J. Am. Chem. Soc.*, 78, 6163–6166 (1956), is a viscous oil which is a mixture of isomers. The pure crystalline isomer is prepared as follows:

A. A mixture of 30 g. of ethyl 2-methyl-3-ethyl-4-ketocyclohexanecarboxylate (all-cis isomer, m.p. 28°–32°), 36 g. of 85% potassium hydroxide, 200 ml. of methanol and 200 ml. of water is stirred and very rapidly heated to the boiling point. After 3 minutes of boiling under reflux, the saponification mixture is cooled, diluted with one liter of water and partially evaporated at 25°–30° to remove most of the methanol. A small amount of insoluble oil is extracted with ether and discarded. The clear aqueous solution is acidified with hydrochloric acid and then extracted three times with methylene dichloride. The combined methylene dichloride solution is dried with anhydrous magnesium sulfate and evaporated to remove solvent as completely as possible. The glassy carboxylic acid is dissolved in a small amount of ether, diluted with hexane, and treated with a few drops of water. The crystalline acid which slowly forms is filtered off and the filtrate is reduced in volume and reworked to produce another crop. A total of 11.8 g. of acid is thus obtained and recrystallization from ether-hexane affords 7.8 g. of 2-methyl-3-ethyl-4-ketocyclohexanecarboxylic acid, m.p. 100°–103°. This all-cis isomer is obtained in its purest form by an additional recrystallization, m.p. 105°–106°.

B. The crude 2-methyl-3-ethyl-4-ketocyclohexanecarboxylic acid described in *J. Am. Chem. Soc.*, 78, 6163–6166 (1956) is prepared by saponification of the corresponding crude ethyl ester. Both compounds are complex mixtures of numerous isomers. Low-temperature recrystallization to isolate the all-cis ester is described elsewhere in this application. The all-cis acid may also be isolated by crystallization as described below.

A 140 g. portion of oily mixed acids is dissolved in 150 ml. of ether plus 350 ml. of hexane. This solution is stirred at 0°C. for 20 hours after which the solid acid is filtered off. This weighs 43 g. and melts at 79°–87°. The acid is recrystallized as described above from 100 ml. of ether plus 300 ml. of hexane to afford 35 g., m.p. 90°–95°. Another recrystallization from ether-hexane finally yields 27 g., m.p. 98°–102°. This is a relatively high quantity sample of the all-cis form of 2-methyl-3-ethyl-4-ketocyclohexanecarboxylic acid and is suitable for such applications as conversion to the 4,4-ethylenedithio derivative, as described above.

IX

Ethyl 2-methyl-3-ethyl-4-ketocyclohexanecarboxylate: all-cis isomer

Crude ethyl 2-methyl-3-ethyl-4-ketocyclohexanecarboxylate (a mixture of isomers) is prepared as described in *J. Am Chem. Soc.*, 78, 6163–6166 (1956). Fifty grams of this ester mixture is dissolved in 350 ml. of pentane plus 20 ml. of ether and the resultant solution is stirred vigorously and cooled slowly to −70°C. The solid which crystallizes at this low temperature is rapidly filtered off with suction onto a pre-cooled funnel and the filter cake is washed with 35 ml. of pentane (pre-cooled to 0°C.). The once-crystallized ester melts above 20°; while still cold the ester is dissolved in 100 ml. of pentane plus 15 ml. of ether and the solution is again stirred and cooled to −70°C. The crystalline solid is filtered off and washed with cold pentane as described above. For final crystallization, the cold solid ester is dissolved in 100 ml. of pentane plus 8 ml. of ether and the stirring, cooling to −70°, and filtering are again performed as described above.

These three low-temperature crystallizations afford 13.4 g. of ethyl 2-methyl-3-ethyl-4-ketocyclohexanecarboxylate as long white prisms, m.p. 28°–32°C. The all-cis configuration is assigned to this isomer on the basis of nuclear magnetic resonance on the ester itself and on products derived therefrom, as described above.

What is claimed is:

1. A compound of the formula:

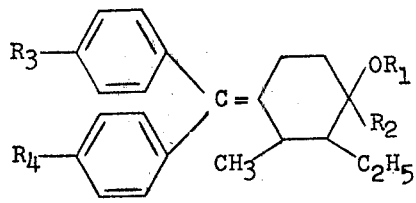

wherein $R_1$ is hydrogen or —COR wherein R is lower alkyl of from 1–5 carbon atoms, $R_2$ is hydrogen, lower alkyl of from 1–5 carbon atoms or lower alkynyl of from 2–5 carbon atoms, $R_3$ and $R_4$ are the same or different hydrogen, lower alkyl of from 1–5 carbon atoms, lower alkoxy of from 1–5 carbon atoms or a lower alkanoyloxy group of from 2–5 carbon atoms.

2. The compound of claim 1, wherein $R_1$ is hydrogen, $R_2$ is lower alkyl and $R_3$ and $R_4$ are hydrogen.

3. The compound of claim 1 wherein $R_1$ is —COR, R is lower alkyl and $R_2$, $R_3$ and $R_4$ are hydrogen.

4. The compound of claim 1 wherein $R_1$ is —COR, R is methyl, and $R_2$, $R_3$ and $R_4$ are hydrogen.

5. The compound of claim 1 wherein $R_1$ is —COR, R is methyl, $R_3$ and $R_4$ are methoxy, and $R_2$ is hydrogen.

6. The compound of claim 1 wherein $R_1$ is —COR, R is pentyl, $R_2$, $R_3$ and $R_4$ are hydrogen.

* * * * *

UNITED STATES PATENT AND TRADEMARK OFFICE
CERTIFICATE OF CORRECTION

PATENT NO. : 3,936,493

DATED : February 3, 1976

INVENTOR(S) : Karmas, George

It is certified that error appears in the above-identified patent and that said Letters Patent are hereby corrected as shown below:

In Column 2, Line 65, (in Example 1), the word "1-Diphenyl-2-methyl-3-ethyl-4-acetoxycyclohexane" should read --- 1-Diphenylmethylenyl-2-methyl-3-ethyl-4-acetoxycyclohexane ---.

In Column 3, Line 54, the word "hydrolyzed at" should read --- hydrolyzed by ---.

In Column 4, Line 14, the word "solution if evaporated" should read --- solution is evaporated ---.

In Column 4, Line 47, the word "in 50 ml. acetic acid" should read --- in 50 ml. of acetic acid ---.

In Column 4, Line 48, the word "p-tolunesulfonic" should read --- p-toluenesulfonic ---.

In Column 5, Line 29, the word "extacted" should read --- extracted ---

In Column 7, Line 65, the word "singleisomer" should read --- single isomer ---.

In Column 8, Line 11, the word "2 g. each cadmium" should read --- 2 g. each of cadmium ---.

In Column 8, Line 22, the word "1-diphenylethylenyl" should read --- 1-diphenylmethylenyl ---.

In Column 8, Line 65, the word "avaporated" should read --- evaporated ---.

In Column 9, Line 13, the word "1-diphenylmetehylenyl" should read --- 1-diphenylmethylenyl ---.

UNITED STATES PATENT AND TRADEMARK OFFICE
CERTIFICATE OF CORRECTION

PATENT NO. : 3,936,493
DATED : February 3, 1976
INVENTOR(S) : Karmas, George

It is certified that error appears in the above-identified patent and that said Letters Patent are hereby corrected as shown below:

In Column 9, Lines 30 and 31, the word "ethylenediethio-cyclohexanecarboxylate" should read --- ethylenedithiocyclohexanecarboxylate ---.

In Column 9, Line 45, the word "12.18" should read --- 12.28 ---.

In Column 10, Line 21, the word "1-]di-(p-anisyl)-2-methyl-3-ethyl-4-ketocyclohexane" should read --- 1-[di-(p-Anisyl) methylenyl]-2-methyl-3-ethyl-4-ketocyclohexane ---.

In Column 11, Line 18, the word "8164" should read --- 8.64 ---.

In Column 12, Line 2, the word "methylene" should read --- methylenyl ---.

In Column 12, Line 20, the word "ethylenedithocyclohexane" should read --- ethylenedithiocyclohexane ---.

In Column 12, Line 43, the word "acidfied" should read --- acidified ---.

In Column 13, Line 7, the word "quantity" should read --- quality ---.

In Column 13, Line 32, the word "stirring." should read --- stirring, ---. (comma not a period after "stirring").

Signed and Sealed this

Ninth Day of November 1976

[SEAL]

Attest:

RUTH C. MASON
Attesting Officer

C. MARSHALL DANN
Commissioner of Patents and Trademarks